United States Patent [19]

Stjernschantz et al.

[11] Patent Number: 5,952,378
[45] Date of Patent: Sep. 14, 1999

[54] METHODS AND MEANS FOR DRUG ADMINISTRATION

[75] Inventors: Johan Stjernschantz; Göran Selén, both of Uppsala, Sweden

[73] Assignee: Pharmacia & Upjohn AB, Stockholm, Sweden

[21] Appl. No.: 08/793,043

[22] PCT Filed: Aug. 24, 1995

[86] PCT No.: PCT/SE95/00962

§ 371 Date: Jun. 5, 1997

§ 102(e) Date: Jun. 5, 1997

[87] PCT Pub. No.: WO96/05840

PCT Pub. Date: Feb. 29, 1996

[30] Foreign Application Priority Data

Aug. 24, 1994 [SE] Sweden ................................. 9402816

[51] Int. Cl.$^6$ .................. A61K 31/215; A61K 31/19
[52] U.S. Cl. ..................... 514/530; 514/573; 514/912
[58] Field of Search ................................ 514/530, 573, 514/912

[56] References Cited

FOREIGN PATENT DOCUMENTS 0286903  10/1988  European Pat. Off. .

OTHER PUBLICATIONS

Eye, vol. 7, 1993, Williamson et al. *Colour Doppler Velocimetry of the Arterial Vasculature of the Optic Nerve Head and Orbit,* pp. 74–79.

*Primary Examiner*—Zohreh Fay
*Attorney, Agent, or Firm*—Dinsmore & Shohl LLP

[57] ABSTRACT

Method and means for delivery of drugs to the optic nerve head and the region surrounding it which comprises contacting the surface of the eye with an effective amount of a drug for treatment of said nerve head and a physiologically acceptable prostaglandin or prostaglandin derivative for enhancing delivery of the drug to the nerve head, in an opththalmologically acceptable carrier.

19 Claims, No Drawings

METHODS AND MEANS FOR DRUG ADMINISTRATION

The invention is concerned with a method of enhanced delivery of drugs to the optic nerve head in the eye, for instance for treatment of glaucoma, utilising prostaglandins. The invention also relates to the use of prostaglandin analogues for the preparation of ophthalmic compositions for such enhanced delivery as well as the compositions as such.

Glaucoma is an eye disorder characterized by increased intraocular pressure, excavation of the optic nerve head and gradual loss of the visual field. An abnormally high intraocular pressure is commonly known to be detrimental to the eye and there are clear indications that in glaucoma the intraocular pressure is the most important factor causing degenerative changes in the retina and the optic nerve head. The exact pathophysiological mechanism of open angle glaucoma is, however, still unknown. Unless treated, glaucoma may lead to blindness, the course of the disease typically being slow with progressive loss of vision.

The intraocular pressure (IOP) can be defined according to the formula:

$$IOP=Pe+(Ft-Fu) \times R \qquad (1)$$

where Pe is the episcleral venous pressure, Ft the formation of aqueous humour, Fu the part of the aqueous humour which exits the eye through the uveoscleral outflow pathway and R is the resistance in the trabecular outflow pathway. The aqueous humour in the anterior and posterior chambers of the eye is formed in the ciliary processes behind the iris. It then flows through the pupil into the anterior chamber and normally exits the eye through the trabecular meshwork and Schlemm's canal into the episcleral veins outside the eye globe. However, part of the aqueous humour may leave the eye through the uveoscleral outflow route. The flow in this route is regarded as only minimally influenced by the intraocular pressure (Bill, 1975).

The intraocular pressure in humans is normally in the range of 12–22 mmHg. At higher values, e.g. above 22 mmHg, there is an increased risk that the eye may be affected. In one particular form of glaucoma, low tension glaucoma, damage may occur at intraocular pressure levels that are within the normal physiological range. The opposite situation is also known, i.e. some individuals may exhibit an abnormally high intraocular pressure without any manifest defects in the visual field or the optic nerve head. Such conditions are usually referred to as ocular hypertension.

Glaucoma treatment can be given by means of drugs, laser or surgery. In drug therapy usually the purpose is to lower either the formation of aqueous humour (Ft) or the resistance to outflow of aqueous humour (R), which according to formula (1) above will result in reduced intraocular pressure; alternatively to increase the outflow of aqueous humour through the uveoscleral route which according to the same formula (1) also reduces the intraocular pressure.

Prostaglandins and typically $PGF_{2\alpha}$ and its derivatives, especially the esters, reduce the intraocular pressure mainly by increasing uveoscleral outflow of aqueous humour (Crawford et al, 1987; Nilsson et al, 1989; Stjernschantz and Resul, 1992; Toris et al, 1993). The use of prostaglandins and their derivatives is described in several patents and patent applications, see for instance U.S. Pat. No. 4,599,353 (Bito), U.S. Pat. No. 4,952,581 (Bito), WO89/03384 (Resul and Stjernschantz), EP 170258 (Cooper), EP 253094 (Goh) and EP 308135 (Ueno).

In addition to reducing the intraocular pressure in glaucoma it would be very desirable to treat the optic nerve head and the ganglion cells of the retina directly, e.g. with neuroprotective agents and vasoactive agents to prevent further loss of nerve cells. A problem, however, is the delivery of the drugs to the site of action, the optic nerve head, which is positioned in the rear part of the eye behind the crystalline lens which is an effective barrier against passive diffusion of compounds posteriorly in the eye, and even in pseudophakic eyes in which the crystalline lens has been removed and exchanged for an intraocular plastic lens, diffusion posteriorly is ineffective. Thus, drugs can only be delivered to the optic nerve head and in amounts sufficiently large by the blood. However, delivering the active drug to the optic nerve head and the retina by systemic administration requires the use of large amounts of drug and furthermore unnecessary systemic side-effects may ensue.

A possible route for delivery of active drugs to the optic nerve head region is through the uveoscleral outflow pathway of aqueous humour. In this route the drug percolates through the ciliary muscle into the suprachoroidal space which extends up to the optic nerve head. There is, however, a well known problem also in this pathway for delivery of drugs. This is comprised by the rich vasculature and high blood flow of the choroid (Alm and Bill, 1987) making absorption of small molecules into the blood very effective. Thus, in spite of the fact that this potential route is known one cannot based on the prior art knowledge expect that the uveoscleral outflow pathway would be a feasible delivery system of drugs to the posterior segment of the eye.

We have now unexpectedly found that it is indeed possible to deliver small drug substances to the optic nerve head region by using prostaglandins for enhancing delivery through the uveoscleral route. Our experiments showed that prostaglandins, exemplified by $PGF_{2\alpha}$-isopropyl ester, applied topically enhanced the backward diffusion of $^3H$-desmetoxyverapamil, a calcium antagonist analogue which was used as a model substance. It is very surprising that verapamil with a rather low molecular weight diffuses up to the optic nerve head in spite of the marked vascularization and blood flow in the choroid. The mechanism of this enhancement of the posterior diffusion of verapamil in the uveoscleral space is not presently known but may be based on a biochemical change of the extracellular matrix in the ciliary muscle brought about by $PGF_{2\alpha}$. However, the invention is not in any way limited to this or any other mechanism.

Thus it is now apparent that prostaglandin derivatives, for instance of class $PGF_{2\alpha}$, its analogues and esters, increase the flux of water and small molecules through the ciliary muscle and may be used therapeutically to enhance the delivery of drugs via the uveoscleral flow pathway to the posterior segment for the treatment of glaucoma. Both the therapeutically active drug and the prostaglandin can be applied topically on the eye provided they penetrate the cornea well enough. In order to fulfil this criteria esters of the prostaglandins are of special importance.

Naturally occurring prostaglandins have the general structure:

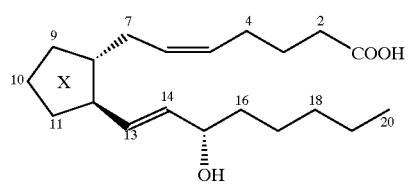

in which the cyclopentyl ring X is

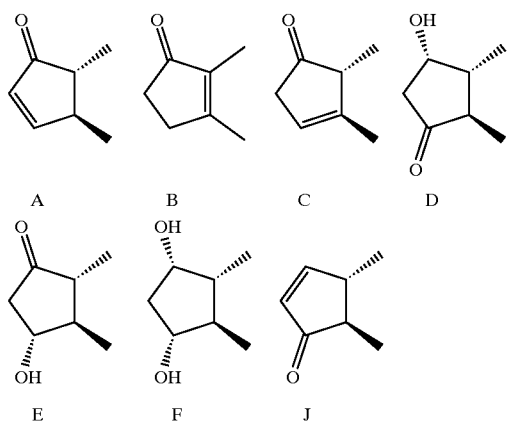

A number of various derivatives have been disclosed in the literature. Modifications of the molecule have been introduced in both of the chains, the alpha chain and the omega chain, as well as in the cyclopentyl ring. An important concept for eliminating undesired side effects, making the derivatives very useful clinically for lowering intraocular pressure, was disclosed in WO90/02553, which is here included by reference. According to this concept a ring substituent was introduced into the omega chain, preferably on carbon 17, giving 17-phenyl-derivatives. Of particular importance are substances exemplified by 13, 14-dihydro-17-phenyl-18, 19, 20-trinor-$PGF_{2\alpha}$-isopropyl ester.

It is generally suggested that the type of derivatives disclosed and exemplified in said WO publication may be of special interest also in connection with the present invention for two reasons: they have been found to be efficient agents for lowering intraocular pressure and they exhibit no or only minor side-effects.

The specific prostaglandin analogue that we have used for exemplifying the concept of the present invention was $PGF_{2\alpha}$-isopropyl ester ($PGF_{2\alpha}$-ie). The choice of model substance does not, however, limit the scope of the invention in any way.

The chemical structure of this substance ($PGF_{2\alpha}$-ie) is

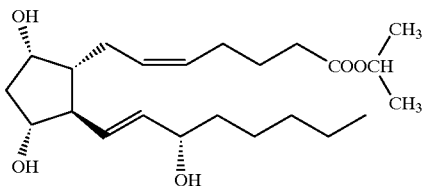

The invention thus relates to the use of prostaglandins for enhancing the delivery of drugs to the optic nerve head for treatment of glaucoma or other diseases of the optic nerve as well as surrounding tissue. The method for enhancing the delivery to the optic nerve head comprises contacting a therapeutically effective amount of a composition containing one or more prostaglandins and one or more drug substances with the eye at certain intervals. The dose contains about 0.1–100 μg, esp. 1–30 μg of the prostaglandin per application. The composition is applied topically on the eye 1–3 times daily or at certain other intervals or periodically. The drug and the prostaglandin substance can alternatively be administered separately. If such a two step administration procedure is chosen the prostaglandin is preferably given first with subsequent administration of the active drug. The two step procedure also includes the situation when the eye is pretreated with the prostaglandin for several days before the active drug is administered alone or combined with additional prostaglandin.

The prostaglandin and the active drug, separately or together, are mixed with an ophthalmologically compatible vehicle known per se. The vehicle that may be employed for preparing compositions according to this invention comprises aqueous solutions, e.g. physiologic saline, oil solutions or ointments. The vehicle may furthermore contain ophthalmologically compatible preservatives like benzalkonium chloride, surfactants, such as polysorbate 80, liposomes or polymers, for example methyl cellulose, polyvinyl alcohol, polyvinyl pyrrolidone, hyaluronic acid or chondroitin sulphate and other glucosamino glucanes. The high molecular weight polymers can be used for increasing the viscosity and the most important substance belonging to this group is hyaluronic acid. Commercially available products especially for ophtalmological applications are Healon® and Healon® GV from Pharmacia AB (Sweden). Furthermore it is also possible to use soluble or insoluble drug inserts. These systems are mentioned merely as examples since various types of administration can be used under the inventive concept, that is to utilise a prostaglandin for increased delivery of a therapeutically active substance to the optic nerve head region.

The invention is also related to the use of prostaglandins as an enhancer substance for the manufacture of ophtalmological compositions comprising a therapeutically active agent to be used for treatment of glaucoma and other diseases of the optic nerve head. Accordingly these compositions comprise one or more prostaglandin substances as enhancer and one or more therapeutically active substances, for instance neuroprotective agents, growth factors and vasoactive agents, for treatment of the optic nerve head in an ophthalmologically compatible carrier. In order to prepare such compositions comprising the prostaglandin as well as the active drug, the substances must be chemically compatible also during long term storage. In cases when combinations of prostaglandins and drugs do not fulfil this criteria, separate compositions comprising the prostaglandin and the drug are prepared and can be provided to the doctor and/or the patient as a kit. Such a kit may comprise two separate containers or one container with separate compartments. Each composition is prepared as described above. Administration into the eye from each of the compartments directly at the same occasion or after given time intervals as well as after mixing are obvious alternatives.

The effective amount of prostaglandin comprises about 0.1–100 μg in preferably about 10–50 μl of the composition.

The amount of the agent used for treatment of the optic nerve head and possibly the ganglion cells of the retina is determined by the need in each specific case and is not a part of this invention which discloses a method for delivery of the substance to the site of action. The substances for treatment are primarily neuroprotective agents, growth factors and their derivatives as well as vasoactive agents that can be used at a variety of doses depending on the formulations.

Such potentially beneficial agents or derivatives thereof, e.g. active fragments, for the treatment of the optic nerve head and the surrounding tissue comprise e.g:

Calcium antagonists such as Verapamil, Nifedipine, Nimodipine, Diltiazem, Nikardipine, Felodipine, Amlodipine, Isradipine;

Angiotensin converting enzyme (ACE) blockers such as Captopril, Enalapril, Lisinopril, Ramipril, Kinapril, Benazepril and Cilazapril;

Phosphodiesterase blockers such as Amrinon, milrinon, IBMX, Theofyllamine:

Nitrates or Nitric oxide generators such as Nitrates, Isorbid Dinitrate, Isorbid Mononitrate, Linsidomine;

Alpha 1-Adrenergic receptor blockers such as Prazosin, Doxazosin, Telazosin;

Smooth muscle relaxing agents such as Diazoxide, Dihydralazin, Hydralazin, Nitroprusside;

Agents for the treatment of vascular disease such as Nicotine alcohole, Inositolnicotinate, Xantinol nicotinate, Cyclomandol;

Beta Adrenergic Agonists such as Salbutamol, Terbutalin, Isoprenalin;

Anticholinergic Agents such as Biperiden, Trihexyphenidyl, Metixen, Procyclidine, Orphenadrine, Atropine, Benzatropine, Homatropine, Scopolamine, BM-5;

Central nervous system active agents such as Heminevrin Hydergine, Cyclomandol

Antioxidants and Radical scavengers such as Lasaroids Ascorbic acid, Glutathione, Dipyridamole, Catalases and their derivatives;

Dopaminergic and serotoninergic agents such as Levodopa, Amantadine, Bromocriptine, Serotonin;

Monoamine oxidase (MAO) inhibitors such as Amytryptyline, Nortryptiline, Selegiline;

Anti-inflammatory agents such as Corticosteroids, Indomethacin, Sulindac, Diclofenac, Piroxicam, Tenoxicam, Ibuprofen, Naproxen, Ketoprofen Growth Factors such as Nerve Growth Factor (NGF), Epidermal Growth Factor (EGF), Insulin-like Growth Factor (IGF), Platelet Derived Growth Factor (PDGF), Transforming Growth Factor (TGF)

Neuropeptides such as substance P, substance K, Enkephalins, Endorphine-like substances, Vasoactive intestinal polypeptide, Calcitonin gene-related peptide, Galanin, Gastrin, Cholecystokinin, and its derivatives, and Other agents such as transglutaminase affecting agents and different interleukins as well as various metabolites of the archidonic acid cascade system, such as certain prostaglandins and leukotrienes.

It has been suggested that prostaglandin derivatives can be used in combination with other types of agents, for instance adrenergic blocking agents, like timolol, for treatment of increased intraocular pressure. Use of prostaglandins in such a combination medicament as an enhancer substance according to the present invention is an obvious alternative embodiment of the present invention.

The invention is illustrated by means of the following non-limiting examples.

Synthesis of Prostaglandin PGF2$_\alpha$ Isopropyl Ester

This compound was prepared from the commercially available corresponding acid, PGF2$_\alpha$. The acid was esterified in acetone with isopropyl iodide in the presence of DBU according to a method described by Grundo R (1980) as a white crystalline product: mp 59–60° C.; yield (77%); R$_f$=0.29 (acetone:EtOAc 1:1); $^1$H NMR (CDCl$_3$) d 0.89 (t, 3H), 1.2 (d, 6H), 1.3 (m, 6H), 1.5 (m, 3H), 1.68 (m, 2H), 1.8 (m,2H), 2.05–2.42 (m, 8H), 2.94 (d, 1H), 3.94 (m, 1H), 4.06 (q, 1H), 4.18 (q, 1H), 5 (sept, 1H), 5.34–5.45 (m, 2H), 5.46–5.52 (q, 1H), 5.54–5.60 (q, 1H); $^{13}$C NMR (CDCl$_3$) d173.39, 135.19, 132.56, 129.72, 129.00, 78.05, 72.99, 72.89, 67.64, 55.83, 50.46, 42.87, 37.27, 34.06, 31.74, 26.63, 25.68, 25.21, 24.90, 22.61, 21.85, 21.84, 14.02.

Use of PGF2$_\alpha$ Isopropyl Ester for enhanced Delivery of $^3$H-desmetoxyverapamil to the Optic Nerve Head.

The experimental technique was based on autoradiography. A cynomolgus monkey was treated topically once daily for five days in one eye with a dose of 2 μg PGF$_{2\alpha}$—ie in an aqueous vehicle containing polysorbate as solubilizer. The other eye received the vehicle only. On the fifth day, approximately 2 hours after administration of PGF$_{2\alpha}$—ie resp vehicle only, 0.6 μg of $^3$H-desmetoxyverapamil (from Amersham) in isotonic saline was applied topically on each eye. The specific activity of the solution containing $^3$H-desmetoxyverapamil was 4.8 mCi/ml corresponding to about 28 μg/ml. While administering the eye drops the monkey was in supine position and anaesthetised with Ketalar/Midazolam.

The monkey was kept anaesthetised for about 4 hours after administration of $^3$H-desmetoxyverapamil. Due to a complication with the anaesthesia the animal had to be changed to an abdominal position, slightly leaning on the left side. Approximately 4 hours after the application of $^3$H-desmetoxyverapamil the animal was sacrificed and the head was processed for autoradiography according to standard techniques.

The localization of the $^3$H-desmetoxyverapamil in the eyes was studied after 6 months photographic exposure of radioactive horizontal sections of the head. Both in the cornea, the aqueous humour, anterior segment and superficially around the eye a much higher radioactivity was found in the control (left) eye, compared to the experimental prostaglandin treated (right) eye. The reason for this is probably the left side position of the monkey after administration of $^3$H-desmetoxyverapamil. In both eyes radioactivity corresponding to $^3$H-desmetoxyverapamil was found as a faint circular line around the choroid up to the optic nerve head. However, the radioactivity in the choroid appeared stronger in the right eye, indicating that proportionally considerably much more $^3$H-desmetoxyverapamil passed into the suprachoroidal space in the prostaglandin treated eye. Thus, it is evident that pretreatment for 5 days with PGF$_{2\alpha}$—ie enhanced the delivery of $^3$H-desmetoxyverapamil to the suprachoroidal space up to the optic nerve head.

The present experiment thus shows firstly that small molecules such as $^3$H-desmetoxyverapamil indeed can diffuse in the suprachoroidal space up to the optic nerve which is most unexpected and secondly, that certain prostaglandins, like PGF$_{2\alpha}$—ie increasing the permeability in the ciliary muscle markedly enhance the diffusion into the suprachoroidal space.

Accordingly, the present invention provides a system for delivery of certain drugs, e.g. neuroprotective or vasoactive drugs to the optic nerve head for the treatment of glaucoma and other diseases or degenerative changes in the optic nerve head and the nerve head region.

REFERENCES

Alm A and Bill A (1987). Ocular Circulation. In: Adler's Physiology of the Eye. (Eds. R A Moses, W M Hart Jr). The CV Mosby Company. PP 183–203.

Bill A (1975). Blood circulation and fluid dynamics in the eye. Physiol. Rew. 55: 383–417.

Crawford K, Kaufman P L, and True Gabelt, B'A (1987). Pilocarpine antagonizes PGF2μ-induced ocular hyptension: Evidence for enhancement of uveoscleral outflow by PGF2μ. Invest. Ophthalmol. Vis Sci p. 11.

Grundo R (1980). A new rapid esterification procedure. Organic Prep. and Proc. Int. 12: 225–228 Organic Prep and Proc Int 12:225–228

Nilsson S F E, Stjernschantz J and Bill A (1987). PGF$_{2\alpha}$ increases uveoscleral outflow. Invest. Ophthalmol. Vis Sci Suppl p. 284.

Stjernschantz J and Resul B (1992). Phenyl Substituted Prostaglandin Analogs for Glaucoma Treatment. Drug of the Future, 17: 691–704.

Toris CB, Camras CB and Yablonski ME (1993). Effects of PhXA41, a New Prostaglandin $F_{2\alpha}$ Analogue, on Aqueous Humor Dynamics in Human Eyes. Ophthalmology 100:1297–1304.

We claim:

1. Method for delivery of drugs to the optic nerve head of an eye and its surrounding region, comprising contacting the surface of the eye with an effective amount of a drug for treatment of the optic nerve head and a physiologically acceptable prostaglandin or prostaglandin derivative for enhancing delivery of the drug to the optic nerve head, in opthalmologically acceptable carrier.

2. Method according to claim 1 wherein a composition comprising the prostaglandin or prostaglandin derivative is administered prior to a composition comprising the drug.

3. Method according to claim 1 wherein the prostaglandin or prostaglandin derivative is of the F-type.

4. Method according to claim 1 wherein the prostaglandin or prostaglandin derivative is an ester.

5. A method for enhancing delivery of a drug to the optic nerve head for treatment of diseases in the optic nerve head region in the eye, comprising contacting the eye with a physiologically acceptable prostaglandin or prostaglandin derivative and contacting the eye with the drug.

6. Method according to claim 5, wherein the prostaglandin is of class $PGF_{2\alpha}$.

7. Method according to claim 6, wherein the prostaglandin is an ester.

8. Method according to claim 7, wherein the prostaglandin derivative is 13,14-dihydro-17-phenyl-18,19,20-trinor-$PGF_{2\alpha}$-isopropyl ester.

9. Method according to claim 1, wherein the prostaglandin is of class $PGF_{2\alpha}$.

10. Method according to claim 1, wherein the prostaglandin derivative is 13,14-dihydro-17-phenyl-18,19,20-trinor-$PGF_{2\alpha}$-isopropyl ester.

11. Method according to claim 1, wherein the drug for treatment of the optic nerve head comprises a neuroprotective agent, a growth factor or a vasoactive agent.

12. Method according to claim 5, wherein the drug for treatment of the optic nerve head comprises a neuroprotective agent, a growth factor or a vasoactive agent.

13. Method according to claim 1, wherein the drug for treatment of the optic nerve head is selected from the group consisting of calcium antagonists, angiotensin converting enzyme blockers, phosphodiesterase blockers, nitrates and nitric oxide generators, alpha 1-adrenergic receptor blockers, smooth muscle relaxing agents, agents for the treatment of vascular disease, beta adrenergic agonists, anticholinergic agents, central nervous system active agents, antioxidants, radical scavengers, dopaminergic agents, serotoninergic agents, monoamine oxidase inhibitors, anti-inflammatory agents, growth factors, neuropeptides and transglutaminase affecting agents.

14. Method according to claim 5, wherein the drug for treatment of the optic nerve head is selected from the group consisting of calcium antagonists, angiotensin converting enzyme blockers, phosphodiesterase blockers, nitrates and nitric oxide generators, alpha 1-adrenergic receptor blockers, smooth muscle relaxing agents, agents for the treatment of vascular disease, beta adrenergic agonists, anticholinergic agents, central nervous system active agents, antioxidants, radical scavengers, dopaminergic agents, serotoninergic agents, monoamine oxidase inhibitors, anti-inflammatory agents, growth factors, neuropeptides and transglutaminase affecting agents.

15. Method according to claim 1, wherein the drug for treatment of the optic nerve head comprises a calcium antagonist.

16. Method according to claim 5, wherein the drug for treatment of the optic nerve head comprises a calcium antagonist.

17. Method according to claim 1, wherein the prostaglandin or prostaglandin derivative is administered in an amount of about 0.1–100 µg.

18. Method according to claim 5, wherein the prostaglandin or prostaglandin derivative is administered in an amount of about 0.1–100 µg.

19. A method for increasing the permeability of a drug in the ciliary muscle to enhance the diffusion of the drug into the suprachoroidal space of the eye to treat the optic nerve head, comprising contacting the surface of the eye with a psychologically acceptable prostaglandin or prostaglandin derivative and contacting the eye with the drug.

* * * * *